(12) United States Patent
Lee

(10) Patent No.: US 11,877,947 B2
(45) Date of Patent: Jan. 23, 2024

(54) EXTERNAL CATHETER SYSTEM

(71) Applicant: Kimberly Lee, Nanticoke, PA (US)

(72) Inventor: Kimberly Lee, Nanticoke, PA (US)

( * ) Notice: Subject to any disclaimer, the term of this patent is extended or adjusted under 35 U.S.C. 154(b) by 0 days.

(21) Appl. No.: 17/216,824

(22) Filed: Mar. 30, 2021

(65) Prior Publication Data

US 2021/0307953 A1 Oct. 7, 2021

Related U.S. Application Data

(60) Provisional application No. 63/005,497, filed on Apr. 6, 2020.

(51) Int. Cl.
| | |
|---|---|
| *A61F 5/451* | (2006.01) |
| *A61F 5/44* | (2006.01) |
| *A61M 1/00* | (2006.01) |
| *A61F 5/453* | (2006.01) |

(52) U.S. Cl.
CPC ............ *A61F 5/451* (2013.01); *A61F 5/4405* (2013.01); *A61F 5/453* (2013.01); *A61M 1/69* (2021.05); *A61M 1/84* (2021.05); *A61M 2202/0496* (2013.01)

(58) Field of Classification Search
CPC ........ A61F 5/451; A61F 5/4405; A61F 5/453; A61M 1/69; A61M 1/84; A61M 2202/0496; A61M 1/87
See application file for complete search history.

(56) References Cited

U.S. PATENT DOCUMENTS

| | | | | |
|---|---|---|---|---|
| 3,353,538 | A | * | 11/1967 | Carrigan ................ A61F 5/453 604/352 |
| 3,905,361 | A | * | 9/1975 | Hewson ............ A61M 16/0493 128/202.16 |
| 3,916,902 | A | * | 11/1975 | Lineberger .............. A61F 5/453 604/352 |
| 4,239,044 | A | * | 12/1980 | Pavlinch ................ A61F 5/453 600/580 |
| 4,655,755 | A | * | 4/1987 | Ruffini .................... A61F 5/453 604/352 |
| 4,759,753 | A | | 7/1988 | Schneider et al. |
| 5,478,334 | A | * | 12/1995 | Bernstein ................ A61F 5/448 604/353 |
| 5,495,858 | A | * | 3/1996 | Steer ....................... A61F 5/448 128/885 |
| 5,662,631 | A | | 9/1997 | Marx |
| 6,068,618 | A | | 5/2000 | Anderson |
| 9,125,752 | B2 | * | 9/2015 | Zeller .................... A61F 5/441 |
| 2003/0136415 | A1 | * | 7/2003 | Lanton, Jr. ............... A61F 5/41 128/842 |

(Continued)

*Primary Examiner* — Benjamin J Klein
*Assistant Examiner* — Hans Kaliher
(74) *Attorney, Agent, or Firm* — Boudwin Intellectual Property Law, LLC; Daniel Boudwin

(57) ABSTRACT

An external catheter system is provided. The system includes an elongated sheath having an open upper end and an open lower end. An inflatable ring is affixed about the open upper end. In some embodiments, the inflatable ring is removably securable to the open upper end of the elongated sheath. An inflation tube is in fluid communication with an interior volume of the inflatable ring. A syringe valve is affixed to a distal end of the inflation tube, wherein the syringe valve operably connects to a syringe. Upon depression of a plunger of the syringe, air is dispensed into the inflatable ring.

13 Claims, 4 Drawing Sheets

(56) References Cited

U.S. PATENT DOCUMENTS

| | | | |
|---|---|---|---|
| 2005/0010181 A1 | 1/2005 | Dolan | |
| 2006/0004332 A1 | 1/2006 | Marx | |
| 2007/0093686 A1* | 4/2007 | Dykers | A61F 5/41 |
| | | | 600/38 |
| 2008/0091155 A1* | 4/2008 | Matter | A61F 5/453 |
| | | | 604/352 |
| 2009/0216206 A1* | 8/2009 | Nishtala | A61F 5/4405 |
| | | | 604/327 |
| 2011/0178484 A1* | 7/2011 | Zivley | A61F 5/453 |
| | | | 604/352 |
| 2014/0171734 A1* | 6/2014 | Kassman | A61H 19/32 |
| | | | 600/38 |
| 2014/0261443 A1* | 9/2014 | Lowenstein | A61M 16/044 |
| | | | 128/207.15 |
| 2015/0320583 A1* | 11/2015 | Harvie | A61F 5/441 |
| | | | 604/351 |

* cited by examiner

EXTERNAL CATHETER SYSTEM

CROSS REFERENCE TO RELATED APPLICATIONS

This application claims the benefit of U.S. Provisional Application No. 63/005,497 filed on Apr. 6, 2020. The above identified patent application is herein incorporated by reference in its entirety to provide continuity of disclosure.

BACKGROUND OF THE INVENTION

The present invention relates to external catheters and other urine drainage systems. More particularly, the present invention pertains to a urine drainage system having an external catheter configured to adjust in diameter via an inflatable ring to secure to a user.

Many men suffer from incontinence, which can cause a series of undesirable health problems, such as dermatitis, skin breakdown, rashes, and the like. In order to avoid such conditions, individuals must apply antibiotics or antifungal medication to relieve symptoms associated with these conditions. Typically, in order to avoid such complications, catheters can be used, however indwelling catheters increase the risk of other conditions, such as urinary tract infections. Alternatively, individuals can use an external catheter, however typical external catheters are uncomfortable and secure via adhesives or elasticity. Other solutions include adult diapers, which can be embarrassing to use, while allow moisture to accumulate in the area, which can potentially lead to dermatitis or rashes. Therefore, an external catheter system that can comfortably secure to a user to allow urine drainage is desired.

In light of the devices disclosed in the known art, it is submitted that the present invention substantially diverges in design elements from the known art and consequently it is clear that there is a need in the art for an improvement to existing external catheter systems. In this regard, the instant invention substantially fulfills these needs.

SUMMARY OF THE INVENTION

In view of the foregoing disadvantages inherent in the known types of external catheters now present in the known art, the present invention provides an external catheter system wherein the same can be utilized for providing convenience for the user when adjusting a diameter of the external catheter to comfortably secure to users of various sizes.

The present system comprises an elongated sheath having an open upper end and an open lower end. An inflatable ring is affixed about the open upper end. In some embodiments, the inflatable ring is removably securable to the open upper end of the elongated sheath. An inflation tube is in fluid communication with an interior volume of the inflatable ring. A syringe valve is affixed to a distal end of the inflation tube, wherein the syringe valve operably connects to a syringe. Upon depression of a plunger of the syringe, air is dispensed into the inflatable ring.

In some embodiments, a pilot balloon is disposed adjacent to and in fluid communication with the syringe valve. In another embodiment, a diameter of the elongated sheath decreases towards the open lower end defining a drainage tube. In other embodiments, the system includes a urine collection bag removably securable to the open lower end. In yet another embodiment, the inflatable ring comprises a rigid outer portion and an inflatable interior portion, wherein the inflatable interior portion is in fluid communication with the inflation tube. In some embodiments, the inflation tube is affixed to a lower side of the inflatable ring. In another embodiment, the syringe comprises a two-way check valve. In other embodiments, the syringe valve is threaded to engage complementary threading disposed on the syringe, such that the syringe is removably securable to the syringe valve. In yet another embodiment, a slot is defined about an upper side of the inflatable ring, the slot configured to frictionally engage the open upper end of the elongated sheath. In some embodiments, the inflatable ring is affixed about an exterior of the open upper end of the elongated sheath. In another embodiment, the open upper end is inserted through a central aperture of the inflatable ring and folded over the inflatable ring to engage the slot.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
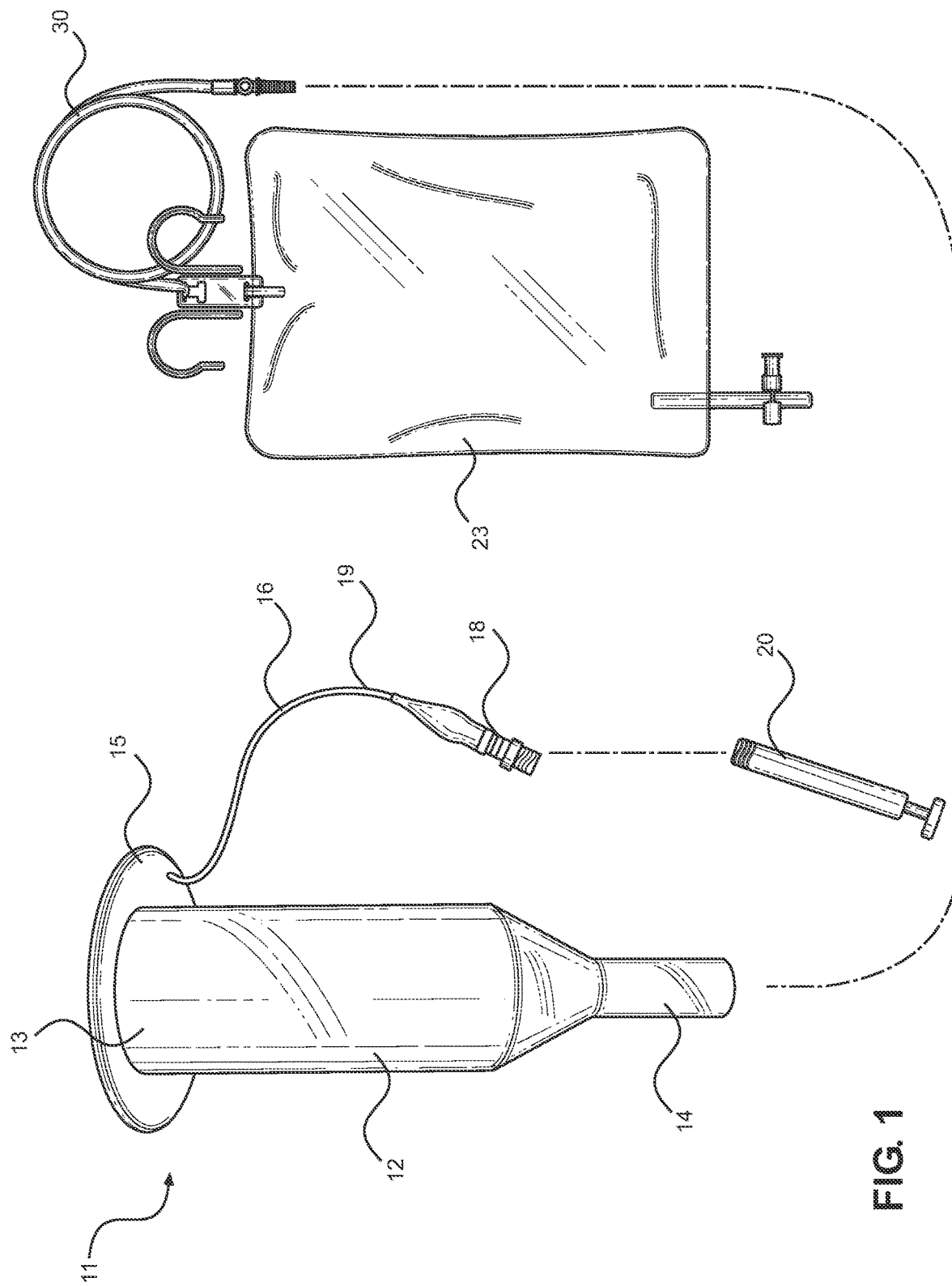
FIG. 1 shows an exploded view of an embodiment of the external catheter system.

Reference is made herein to the attached drawings. Like reference numerals are used throughout the drawings to depict like or similar elements of the external catheter system. The figures are intended for representative purposes only and should not be considered to be limiting in any respect.

Referring now to FIG. 1, there is shown an exploded view of an embodiment of the external catheter system. The external catheter system 11 comprises an elongated sheath 12 having an open upper end 13 opposite an open lower end 14. The elongated sheath 12 is dimensioned to receive a patient's penis therein. In the shown embodiment, the diameter of the elongated sheath 12 comprises an oversized diameter for the typical penis dimensions to ensure the patient's comfort is maximized as the elongated sheath 12 does not uncomfortably constrict to secure to the patient. The elongated sheath 12 is contemplated to comprise a flexible and medical grade plastic or latex material, such that the open upper end 13 can be folded over itself to secure to an inflatable ring 15 as further described elsewhere herein. The open lower end 14 of the elongated sheath 12 is dimensioned to removably secure to tubing 30 of a urine collection bag 23 to form a watertight seal. In the shown embodiment, the tubing 30 removably secures via typical medical grade fittings to ensure a seal is created. The tubing 30 is in fluid communication with an interior of the urine collection bag 23, such that urine expelled from the patient into the elongated sheath 12 exits through the open lower end 14 and into the urine collection bag 23 via the tubing 30.

In some embodiments, the inflatable ring 15 is integrally affixed to the open upper end 13 of the elongated sheath 12, however, in alternate embodiments, the inflatable ring 15 is removably securable to the elongated sheath 12 to allow the elongated sheath 12 to be replaced as needed, such as for cleaning or in the event of damage to the elongated sheath 12. Additionally, the removably securable nature of the inflatable ring 15 provides the benefit of reduced form factor when storing the external catheter system 11 between uses. The inflatable ring 15 further comprises an inflation tube 16 in fluid communication with an interior volume of the inflatable ring 15. A syringe valve 18 is disposed on a distal end 19 of the inflation tube 16, wherein the syringe valve 18 is configured to operably connect to a syringe 20 to transfer air through the inflation tube 16 into the interior volume of the inflatable ring 15. In this manner, as air is introduced into the inflatable ring 15, the inflatable ring 15 constricts about the open upper end 13 of the elongated sheath 12, thereby functionally decreasing the diameter of the open upper end 13. This allows the user to comfortably secure the elongated sheath 12 to a patient. In some embodiments, the syringe valve 18 comprises a two-way valve allowing a user to either inject air via the syringe 20 into the inflatable ring 15 or remove air from the inflatable ring 15 to deflate the inflatable ring 15 upon actuation of a plunger of the syringe 20. In this manner, the user can readily inflate or deflate the inflatable ring 15 as needed to secure or remove the external catheter system 11 from a patient.

Figure 2:
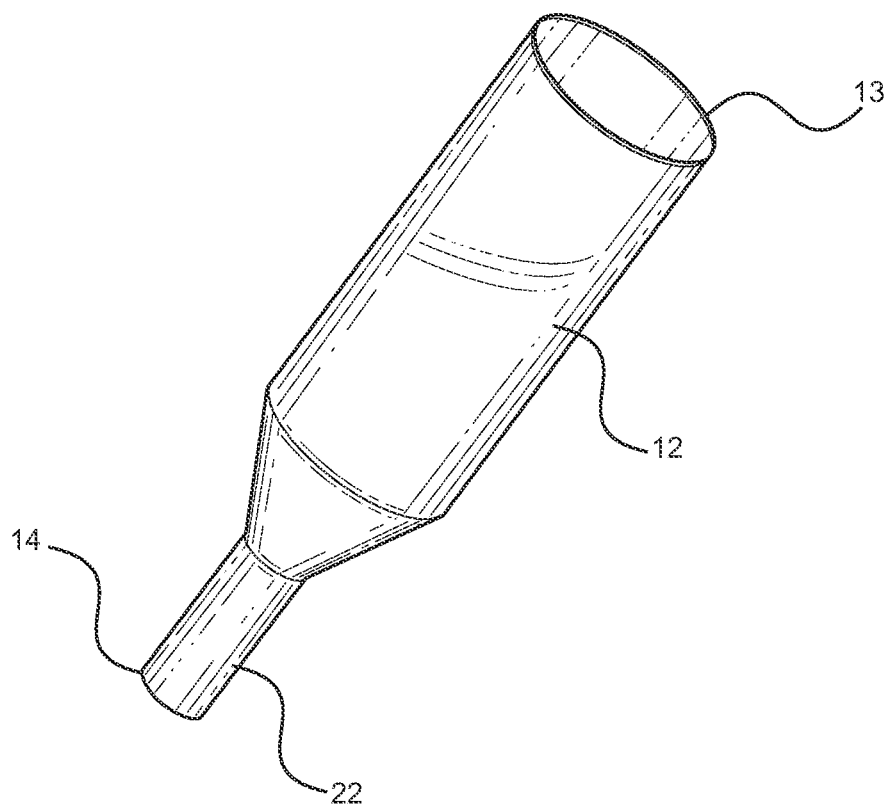
FIG. 2 shows a perspective view of the elongated sheath of an embodiment of the external catheter system.

Referring now to FIG. 2, there is shown a perspective view of the elongated sheath of an embodiment of the external catheter system. The elongated sheath 12 comprises a flexible and fluid impermeable material to prevent leaks from the interior of the elongated sheath 12. In some embodiments, the elongated sheath 12 further comprises an elastic material to expand to accommodate movement of the patient stretching the elongated sheath 12. Additionally, the elongated sheath 12 is contemplated to comprise a medical grade plastic or latex material to increase patient comfort and reduce the risk of allergic reactions. The elongated sheath 12 comprises an open upper end 13, wherein the open upper end 13 comprises a flexible material configured to allow the open upper end 13 to fold outwardly from a longitudinal axis of the elongated sheath 12 to form a cuff which can removably secure to the inflatable ring as further described elsewhere herein. In the shown embodiment, the elongated sheath 12 tapers inwardly towards the open lower end 14 to define a drainage tube 22 at the open lower end 14. The drainage tube 22 is configured to removably secure to the tubing of the urine collection bag with a watertight seal to prevent leaks from the open lower end 14.

Figure 3:
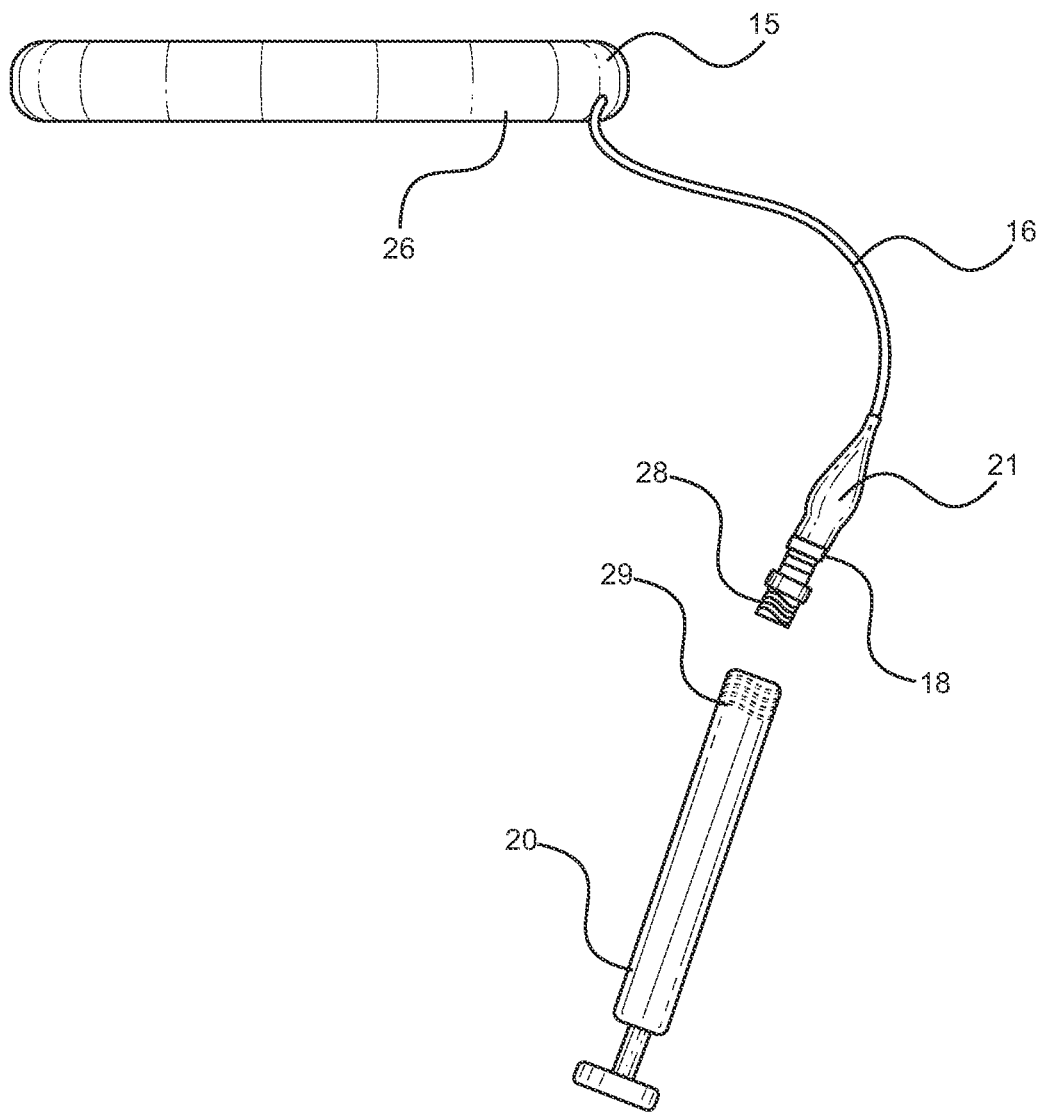
FIG. 3 shows a side view of the inflatable ring of an embodiment of the external catheter system.

Referring now to FIG. 3, there is shown a side view of the inflatable ring of an embodiment of the external catheter system. In the illustrated embodiment, the inflation tube 16 is affixed to the inflatable ring 15 on a lower side 26 thereof, such that the inflation tube 16 is maintained away from the patient when the external catheter system is secured to the patient. In this manner, the patient's comfort is maximized as the inflation tube 16 does not press into the patient during use. In the shown embodiment, the syringe valve 18 is in fluid communication with a pilot balloon 21 affixed to the syringe valve 18. The pilot balloon 21 is configured to inflate as air is injected via the syringe 20 to allow the user to gauge the amount of pressure introduced into the inflatable ring 15. In this manner, the user can prevent overfilling the inflatable ring 15, which could cause the inflatable ring 15 to rupture, possibly injuring the patient. In the shown embodiment, the syringe valve 18 comprises threading 28 thereon, wherein the threading 28 is configured to engage complementary threading 29 disposed on the syringe 20. The threading 28 may be internally or externally disposed on the syringe valve 18 to engage complementary threading 29 on the exterior or interior of the syringe 20, respectively. In this manner, the user can removably secure the syringe 20 to the syringe valve 18 during operation of the inflatable ring 15 to minimize leaks from the syringe valve 18. Similarly, in this fashion, the syringe 20 is maintained on the syringe valve 18 during operation.

Figure 4:
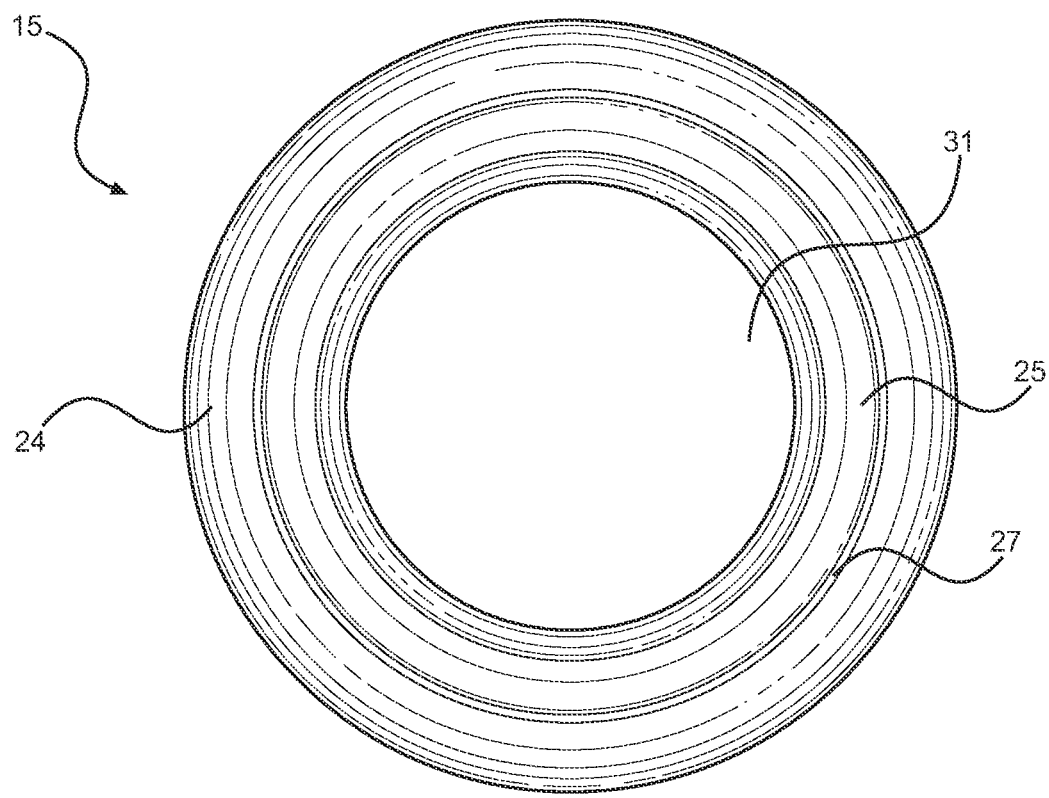
FIG. 4 shows a top plan view of the inflatable ring of an embodiment of the external catheter system.

Referring now to FIG. 4, there is shown a top plan view of the inflatable ring of an embodiment of the external catheter system. In the illustrated embodiment, the inflatable ring 15 further comprises a slot 27 disposed annularly about an upper side of the inflatable ring 15, wherein the slot 27 is dimensioned to frictionally engage the open upper end of the elongated sheath therein. In operation, in the shown embodiment, the open upper end of the elongated sheath is inserted through an aperture 31 disposed through the inflatable ring 15, wherein the open upper end is then folded over and inserted into the slot 27 to secure the elongated sheath to the inflatable ring 15. In the illustrated embodiment, the slot 27 further serves to distinguish the inflatable ring 15 into an interior portion 25 and an exterior portion 24. In some embodiments, the exterior portion 24 comprises a rigid material configured to retain the shape of the inflatable ring 15 when not inflated, whereas the interior portion 25 comprises an inflatable portion in fluid communication with the inflation tube. In this manner, the interior portion 25 functionally decreases the diameter of the aperture 31 when the interior portion 25 is inflated to secure the inflatable ring 15 to a patient. In alternate embodiments, an entirety of the inflatable ring 15 comprises an inflatable structure with a defined slot 27 disposed within the upper side thereof to provide an anchor for the open upper end of the elongated sheath.

In one use, the inflatable ring 15 is affixed to the elongated sheath and the patient's penis is inserted into the elongated sheath. A syringe is affixed to the syringe valve and delivers air through the inflation tube into the inflatable ring 15 to functionally decrease the diameter of the open upper end of the elongated sheath, thereby securing the external catheter system to the patient. A urine collection bag is connected to the open lower end of the elongated sheath via tubing connected to the urine collection bag, such that any urine expelled through the open lower end is directed to the interior of the urine collection bag. Should the elongated sheath need to be replaced, the user can deflate the inflatable ring 15 by withdrawing air through the inflation tube via the syringe, removing the external catheter system, and disconnecting the elongated sheath from the inflatable ring 15. A new elongated sheath can then be secured to the inflatable ring 15 and resecured to the patient. In some embodiments, the elongated sheath is secured within the slot 27 defined along the upper side of the inflatable ring 15. In this manner, the patient can utilize a comfortable, reusable, and replaceable external catheter system in a safe and efficient fashion.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An external catheter system, consisting of:
 a flexible elongated sheath having an open upper end and an open lower end;
 an inflatable ring affixed about an exterior of the open upper end;
 wherein the inflatable ring comprises a unitary construction having a rigid exterior ring portion and an inflatable interior ring portion;
 wherein the inflatable interior ring portion is disposed on an interior surface of the rigid exterior ring portion, such that the rigid exterior ring portion and the inflatable interior ring portion are disposed in a coplanar orientation;
 an inflation tube in fluid communication with an interior volume of the inflatable interior ring portion of the inflatable ring;
 a syringe valve affixed to a distal end of the inflation tube, wherein the syringe valve is configured to operably connect to a syringe;
 whereupon depression of a plunger of the syringe, air is dispensed into the inflatable ring;
 further comprising a pilot balloon disposed adjacent to and in fluid communication with the syringe valve;
 wherein the syringe valve comprises a two-way check valve; and
 further comprising a urine collection bag removably securable to the open lower end.

2. The external catheter system of claim 1, wherein a diameter of the elongated sheath decreases towards the open lower end defining a drainage tube.

3. The external catheter system of claim 1, wherein the inflation tube is affixed to a lower side of the inflation ring.

4. The external catheter system of claim 1, wherein the syringe valve is threaded to engage complementary threading disposed on the syringe, such that the syringe is removably securable to the syringe valve.

5. The external catheter system of claim 1, wherein the inflatable ring is affixed about an exterior of the open upper end of the elongated sheath.

6. An external catheter system, consisting of:
 a flexible elongated sheath having an open upper end and an open lower end;
 an inflatable ring removably securable about an exterior of the elongated sheath such that the open upper end extends through an entirety of the inflatable ring;
 a slot disposed about a circumference of the inflatable ring along an upper side thereof,
 wherein the slot is dimensioned to frictionally engage the open upper end of the elongated sheath therein;
 whereupon securement of the inflatable ring to the elongated sheath, the upper side of the inflatable ring is disposed perpendicular to each of a longitudinal axis of the elongated sheath and a sidewall of the elongated sheath, wherein the sidewall is defined between the open upper end and the open lower end;
 an inflation tube in fluid communication with an interior volume of the inflatable ring;
 a syringe valve affixed to a distal end of the inflation tube, wherein the syringe valve is configured to operably connect to a syringe;
 whereupon depression of a plunger of the syringe, air is dispensed into the inflatable ring;
 further comprising a pilot balloon disposed adjacent to and in fluid communication with the syringe valve; and
 further comprising a urine collection bag removably securable to the open lower end.

7. The external catheter system of claim 6, wherein a diameter of the elongated sheath decreases towards the open lower end defining a drainage tube.

8. The external catheter system of claim 6, wherein the inflatable ring comprises a rigid exterior ring portion and an inflatable interior ring portion disposed on an interior surface of the rigid exterior ring portion, the inflatable interior ring portion disposed coplanar relative to the rigid exterior ring portion, wherein the inflatable interior portion is in fluid communication with the inflation tube.

9. The external catheter system of claim 6, wherein the inflation tube is affixed to a lower side of the inflation ring.

10. The external catheter system of claim 6, wherein the syringe valve comprises a two-way check valve.

11. The external catheter system of claim 6, wherein the syringe valve is threaded to engage complementary threading disposed on the syringe, such that the syringe is removably securable to the syringe valve.

12. The external catheter system of claim 6, wherein the elongated sheath removably secures to the inflatable ring via inserting the open upper end through a central aperture of the inflatable ring and folding the open upper end to engage the slot.

13. The external catheter system of claim 8, wherein the slot is defined between the rigid exterior ring portion and the inflatable interior ring portion.

* * * * *